Figure 1:
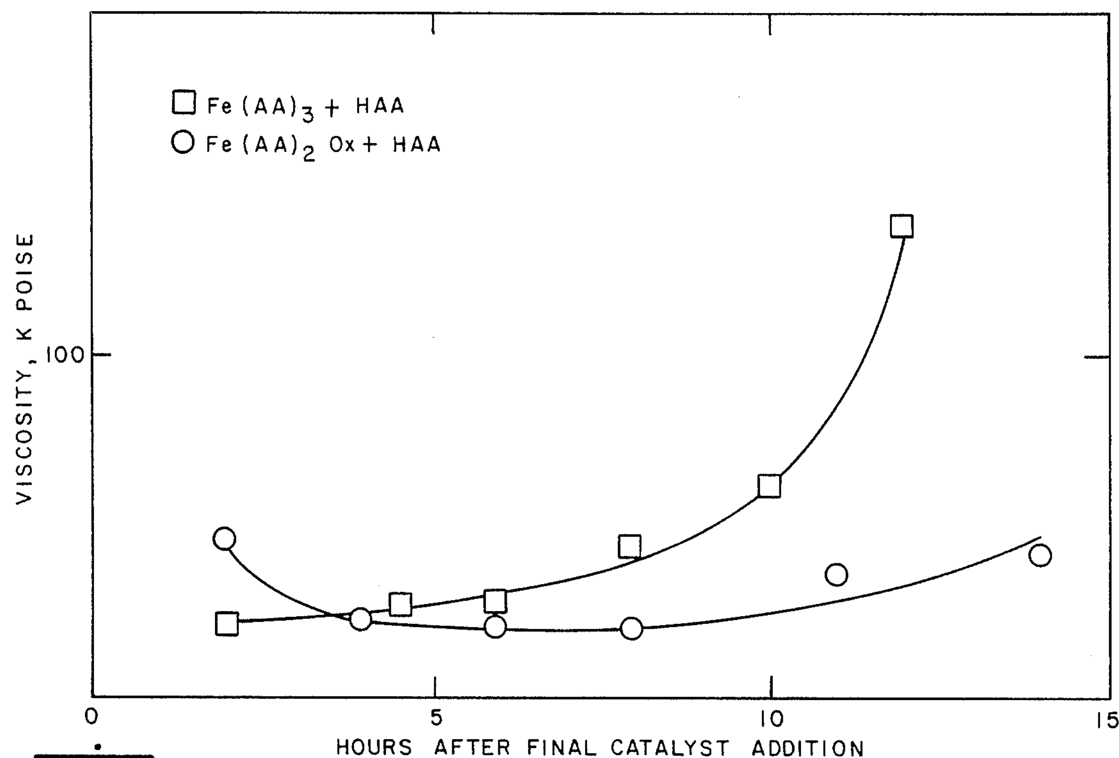

United States Patent [19]

Oberth et al.

[11] Patent Number: 4,871,854

[45] Date of Patent: Oct. 3, 1989

[54] CURE CATALYST FOR POLYURETHANES

[75] Inventors: Adolf E. Oberth; Julius Rothenstein, both of Fair Oaks, Calif.

[73] Assignee: The United States of America as represented by the Secretary of the Air Force, Washington, D.C.

[21] Appl. No.: 392,995

[22] Filed: Jun. 28, 1982

[51] Int. Cl.[4] .......... C07F 15/02

[52] U.S. Cl. .......... 546/7

[58] Field of Search .......... 149/19.4; 546/7

[56] References Cited

U.S. PATENT DOCUMENTS

| | | | |
|---|---|---|---|
| 3,036,022 | 5/1962 | Stewart et al. | 546/7 |
| 3,197,436 | 7/1965 | Block et al. | 546/7 |
| 3,287,455 | 11/1966 | Malkin et al. | 546/7 |
| 4,000,023 | 12/1976 | Oberth et al. | 149/19.4 |
| 4,050,969 | 9/1977 | Oberth | 149/19.4 |

OTHER PUBLICATIONS

Bailar et al., *Comprehensive Inorganic Chemistry,* vol. 3, pp. 1044–1045, Pergamon Press (1973) Oxford.

*Primary Examiner*—Edward A. Miller

*Attorney, Agent, or Firm*—Charles E. Bricker; Donald J. Singer

[57] ABSTRACT

Described herein is an improved cure catalyst, ferric-bis(acetylacetonato)oxinate, for urethane polymers derived form polyetherdiols and thiols, polybutadienediols and triols, polyesters and the like.

3 Claims, 1 Drawing Sheet

CURE CATALYST FOR POLYURETHANES

RIGHTS OF THE GOVERNMENT

The invention described herein may be manufactured and used by or for the Government of the United States for all governmental purposes without the payment of any royalty.

This invention relates to solid propellants, and in particular to cure catalysts for polyurethane propellant binders.

Ferric-tris(acetylacetonate) is a known cure catalyst for polyurethanes. It has been employed as a cure catalyst for polyurethane binders in solid propellant systems, as disclosed, for example, in U.S. Pat. No. 4,000,023. It has been found that reactive impurities in certain propellant formulations tend to destroy at least a portion of the ferric-tris(acetylacetonate), thereby endangering the cure or reproducibility of mechanical properties.

It is therefore an object of the present invention to provide an improved cure catalyst.

It is another object of this invention to provide a method for producing an improved cure catalyst.

Figure 2:
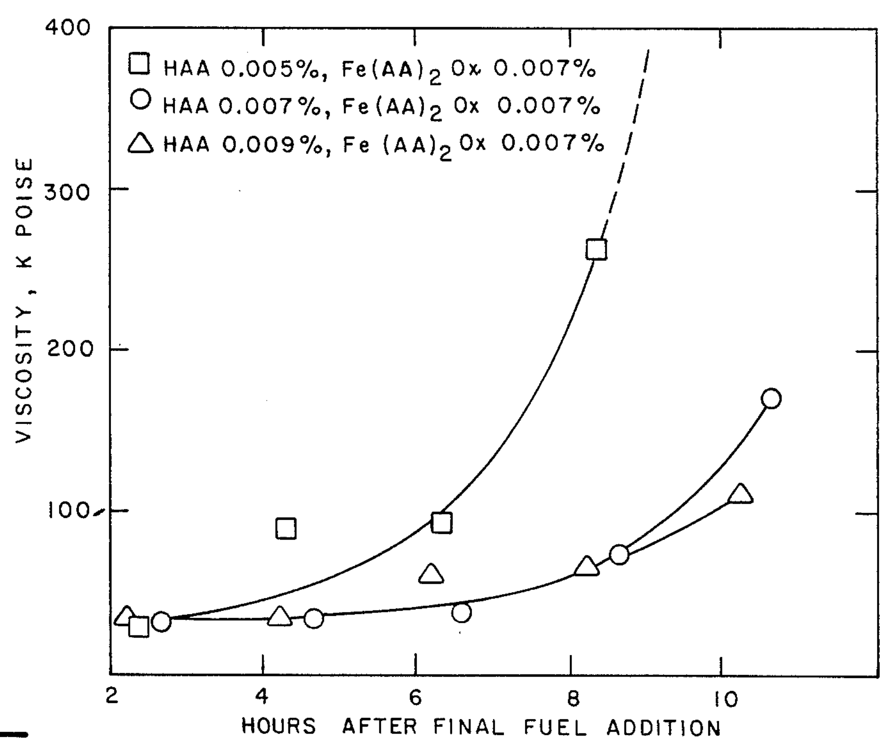

Other objects and advantages of this invention will be apparent from the description which follows, and from the drawing in which:

FIG. 1 illustrates the effect of the cure catalyst of this invention on viscosity buildup, as compared to ferric-tris(acetylacetonate); and FIG. 2 illustrates the effect of different concentrations of catalyst modifier with the catalyst of this invention.

In accordance with the present invention, there is provided an improved cure catalyst, ferric-bis-(acetylacetonato) oxinate. This new compound is somewhat less active than ferric-tris(acetylacetonate), but is chemically more stable, which makes it useful for certain propellant formulations wherein reactive impurities tend to destroy the catalyst.

The compound of this invention is prepared by combining ferric chloride with acetylacetone and 8-hydroxyquinoline in a suitable liquid medium and thereafter adding a base, such as an alkali metal hydroxide to precipitate out the ferric-bis(acetylacetonato) oxinate, in accordance with the general reaction scheme set forth below:

$$FeCl_3+2HAA+HOx+3MOH \rightarrow Fe(AA)_2Ox+3MCl+3H_2O$$

wherein AA is the acetylacetonate ion

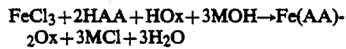

Ox is the 8-hydroxyquinoline ion

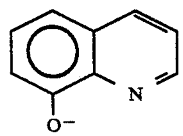

M is an alkali metal, such as lithium, sodium or potassium, HAA is acetylacetone, HOx is 8-hydroxyquinoline, and $Fe(AA)_2Ox$ is ferric-bis(acetylacetonato)oxinate.

Ferric-bis(acetylacetonato)oxinate may be employed for the catalysis of urethane polymers derived from polyetherdiols, thiols, etc., such as polyethylene glycol (PEG), polyoxypropylene diol (PPG), and the like, polybutadiene (HTPB), polyesters such as neopentylglycol azelate-polyester (NPGA) with isocyanates as curatives. The ferric-bis(acetylacetonato)oxinate is employed in a catalytic amount. Generally, such an amount is in the approximate range of 0.01 to 0.10 weight percent of the polyurethane composition.

Acetylacetone (HAA) may be employed to modify the catalytic action of the ferric-bis(acetylacetonato)oxinate. In general, the amount of HAA can range from about 50 to 200% of the cure catalyst.

The ferric-bis(acetylacetonato)oxinate is particularly useful for the catalysis of polyurethane binders in solid propellant compositions. The propellants may contain components such as cyclotetramethylenetetranitramine (HMX), cyclotrimethylenetrinitramine (RDX) trimethylolethane trinitrate (TMETN), aluminum, oxidizing agents, plasticizers, stabilizers, and the like. The amount of polyurethane binder in such propellant compositions can range from about 10 to about 25 weight percent of the total composition. The ferric-bis-(acetylacetonato)oxinate responds to acetylacetone as a catalyst modifier just as does ferric-tris(acetylacetonate). The potlife of propellant compositions containing ferric-bis(acetylacetonato)oxinate is increased significantly as compared to compositions containing ferric-tris(acetylacetonate), and the initial (end of mix) viscosity is approximately the same as with ferric-tris(acetylacetonate). Neither mechanical properties nor propellant aging are significantly affected when ferric-bis-(acetylacetonato)oxinate is employed in place of ferric-tris(acetylacetonate). Because potlife is increased, ferric-bis(acetylacetonato)oxinate can be employed in higher concentrations and still exhibit good potlife, thereby reducing the chance of soft cures, i.e., incomplete cures, in the presence of small amounts of catalyst-consuming or deactivating impurities.

The following examples illustrate the invention.

EXAMPLE I

Preparation of Ferric-bis(acetylacetonato)oxinate

To a solution of 200 g (2 moles) acetylacetone, 145 g (1 mole) 8-hydroxyquinoline and 162 g (1 mole) ferric chloride, in 2 liters of acetone, were added slowly, with stirring, a solution of 168 g (2.9 moles) KOH in 336 g water. Following addition of the KOH, 2 liters of water were added, with stirring, to precipitate the catalyst. The catalyst was filtered, air-dried at ambient temperature and then dried over phosphorus pentoxide under a vacuum at 38° C. Yield: 350 g of ferric-bis-(acetylacetonato)oxinate, 88% of theory.

EXAMPLE II

A series of propellants was prepared, each containing 84% total solids, which included cyclotetramethylenetetranitramine(HMX) and ammonium perchlorate (AP) in a 4:1 weight ratio and 19% aluminum powder. The binder consisted of polyethyleneglycol having a molecular weight of approximately 4000 (PEG-4000), trimethylol propane (TMP) crosslinker, and hexamethylene diisocyanate (HDI) curing agent, plasticized 75% with bis(2-fluoro-2,2-dinitro-ethyl)formal (FEFO).

Other ingredients in the formulation included a bonding agent which is a tetraethylenepentamine-acrylonitrile adduct partially neutralized with p-toluene sulfonic acid (TEPAN-T), diphenylamine (DPA) stabilizer, and acetylacetone (HAA) catalyst modifier. Certain of the propellant formulations were catalyzed with ferric-tris-(acetylacetonate)[$Fe(AA)_3$] and others were catalyzed with the catalyst of this invention, ferric-bis-(acetylacetonato)oxinate [$Fe(AA)_2Ox$].

The following procedure was employed with all the formulations:

a. A submix consisting of the FEFO, most of the PEG-4000 and part of the DPA was mixed under vacuum.

b. A solution containing 50–60% of the catalyst ("catalyst split") in 10–20% of the required amount of HDI ("HDI Split") was added to the submix and mixed.

c. The aluminum and the remainder of the DPA was added and mixed.

d. The AP was added, with mixing.

e. The HMX was added in two portions, each with mixing.

f. A solution containing the TMP and the remainder of the PEG-4000 in the TEPAN-T was added and mixed.

g. The remainder of the catalyst, the HAA and the remainder of the HDI were combined, then added to the previous mixture.

h. Following a suitable period of mixing, the propellant was cast into suitable container, then cured at 110° F. for 5–8 days.

The mechanical properties and viscosities of the above formulations are given in Table I below.

TABLE I

| No | Wt. % | Cat. Split | HDI Split | Viscosity K poise 2 hr | Viscosity K poise 8 hr | Mech Prop at 77° F. $\sigma_m$, psi | $\epsilon_m$, % | $\epsilon_b$, % | $E_o$, psi |
|---|---|---|---|---|---|---|---|---|---|
| | $Fe(AA)_3$/HAA | | | | | | | | |
| 1 | 0.006/0.006 | 1/1 | 10/90 | 30 | off scale | 87 | 22 | 22 | 458 |
| 2 | .005/.005 | 1/1 | 10/90 | 25 | 400 | 87 | 24 | 25 | 429 |
| 3 | .005/.005 | 3/2 | 15/85 | 39 | 430 | 80 | 20 | 21 | 470 |
| 4 | .005/.005 | 1/1 | 20/80 | 30 | off scale | 79 | 19 | 20 | 477 |
| 5 | .004/.004 | 1/1 | 10/90 | 36 | off scale | 104 | 20 | 21 | 596 |
| 6 | .004/.004 | 1/1 | 15/85 | 33 | off scale | 89 | 19 | 20 | 525 |
| 7 | .003/.003 | 1/1 | 15/85 | 26 | 500 | 95 | 21 | 22 | 512 |
| 8 | .003/.005 | 1/1 | 15/85 | 22 | 85 | 87 | 22 | 23 | 497 |
| 9 | .003/.005 | 1/1 | 10/90 | 110 | off scale | 83 | 23 | 24 | 431 |
| 10 | .002/.002 | 1/1 | 10/90 | offscale | | 85 | 27 | 29 | 416 |
| | $Fe(AA_2)Ox$/HAA | | | | | | | | |
| 11 | .006/.006 | 1/1 | 15/85 | 20 | 90 | 92 | 21 | 22 | 521 |
| 12 | .006/006 | 1/1 | 15/85 | 19 | 135 | 93 | 21 | 21 | 530 |
| 13 | .006/.008 | 1/1 | 15/85 | 22 | 53 | 89 | 23 | 24 | 462 |
| 14 | .006/.006 | 1/1 | 20/80 | 20 | 59 | 83 | 20 | 22 | 508 |
| 15 | .005/.005 | 1/1 | 10/90 | 70 | off Scale | 100 | 21 | 21 | 570 |
| 16 | .005/.005 | 1/1 | 15/85 | 49 | 765 | 93 | 21 | 21 | 528 |
| 17 | .005/.005 | 1/1 | 20/80 | 19 | 102 | 87 | 22 | 23 | 455 |

EXAMPLE III

Two propellant formulations, prepared as in Example II, one employing $Fe(AA)_3$ as the catalyst and the other employing $Fe(AA)_2Ox$ as the catalyst, were tested for mechanical properties. The results of these tests are given in Table II below. Additionally, the viscosity of each formulation was checked at intervals following the final addition of catalyst. A comparison of the effect of the cure catalyst and viscosity buildup is shown in FIG. 1. Viscosity was taken at 10 Kdynes/cm$^2$ and 100° F.

TABLE II

| Catalyst System | Mechanical Properties $\sigma_m$, psi | $\epsilon_m$, % | $E_o$, psi | Time to 100 Kpoise, hr |
|---|---|---|---|---|
| $Fe(AA)_2Ox$ + HAA | 109 | 22 | 631 | 15 |
| $Fe(AA)_3$ + HAA | 110 | 17 | 765 | 11.3 |

The above data illustrate that the mechanical properties of the cured propellants are not adversely affected by replacing $Fe(AA)_3$ with $Fe(AA)_2Ox$. FIG. 1 illustrates the increased potlife afforded by $Fe(AA)_2Ox$.

EXAMPLE IV

Effect of Different Amounts of Catalyst Modifier on Viscosity Buildup

A series of propellant formulations were prepared as described above using 0.007% $Fe(AA)_2Ox$ (based on the total propellant weight) and varying amounts of HAA catlyst modifier (also based on the total propellant weight). The viscosity of each formulation was measured at intervals of about 2 hours following the final addition of catalyst. The results are shown in FIG. 2.

As will be evident to those skilled in the art, modifications of the present invention can be made in view of the foregoing disclosure without departing from the spirit and scope of the invention

We claim:

1. A method for producing ferric-bis(acetylacetonato)oxinate which comprises combining a ferric halide, acetylacetone and 8-hydroxyquinoline in a molar ratio of 1:2:1, respectively, in a suitable liquid media, adding sufficient base to neutralize the resulting mixture and precipitate the product and recovering said product.

2. The method of claim 1 wherein said liquid media is acetone.

3. The method of claim 1 wherein said base is an alkali metal hydroxide.

* * * * *